US005610240A

United States Patent [19]
Hogt et al.

[11] Patent Number: 5,610,240
[45] Date of Patent: *Mar. 11, 1997

[54] ANTI-REVERSION COAGENTS FOR RUBBER VULCANIZATION

[75] Inventors: Andreas H. Hogt, Enschede; Auke G. Talma, Bathmen; Rudolf F. de Block; Rabindra N. Datta, both of Deventer, all of Netherlands

[73] Assignee: Akzo Nobel NV, Arnhem, Netherlands

[ * ] Notice: The term of this patent shall not extend beyond the expiration date of Pat. No. 5,426,155.

[21] Appl. No.: 413,567

[22] Filed: Mar. 30, 1995

Related U.S. Application Data

[63] Continuation of Ser. No. 50,049, filed as PCT/EP91/02048, on Oct. 29, 1991, published as WO92/07904, on May 14, 1992 now Pat. No. 5,426,155.

[30] Foreign Application Priority Data

Oct. 29, 1990 [EP] European Pat. Off. .............. 90202864

[51] Int. Cl.$^6$ ...................................................... C08F 8/34
[52] U.S. Cl. .................... 525/332.6; 525/332.7; 525/375
[58] Field of Search ............................ 525/332.6, 332.7, 525/375

[56] References Cited

U.S. PATENT DOCUMENTS

| | | | |
|---|---|---|---|
| 3,297,713 | 1/1967 | Lado | 260/326.3 |
| 3,974,163 | 8/1976 | Coran et al. | 260/281 |
| 4,323,662 | 4/1982 | Oba et al. | 528/281 |
| 5,426,155 | 6/1995 | Hogt et al. | 525/332.6 |

FOREIGN PATENT DOCUMENTS

| | | |
|---|---|---|
| 0738500 | 7/1966 | Canada . |
| 0191931 | 8/1986 | European Pat. Off. . |
| 0345825 | 12/1989 | European Pat. Off. . |
| 0410152 | 1/1991 | European Pat. Off. . |
| 1257913 | 4/1960 | France . |
| 0182355 | 7/1988 | Japan . |
| 0286445 | 11/1988 | Japan . |

OTHER PUBLICATIONS

"Rubber Microstructure and Reversion". Nordsiek, Dr. K. H., *Rubber World*, 197, pp. 30–38, 1987.
"Vulcanization with Maleimides," Tawney, P.O. *Journ of Applied Poly. Sci.*, vol. 8, pp. 2281–2297, 1964.
"Vulcanization of cis-1,4-isopropene rubber by deryicates of maleimide under the action of high temperature and radiation" Praschinka, A. S. et al., *Kauchuk i Rezina*, No. 3, pp. 10–12, Mar. 1974.
"High–temperature vulcanisation of unsaturated rubbers by thio derivatives of maleimide," Prashchikina, A. S. et al, *Kauchuk i Rezina*, No. 3, pp. 16–20, 1975.
"The Synthesis of biscitraconimides and polybiscitraconimides" Galanti, A. V. and Scola, D. A., Journ of Polym Sci. Polymer Chemistry Edition, vo. 19, pp. 451–475 (1981).
"The Synthesis of biscitraconimides," Galanti, A. V. and Scola, D. A., Journ. of Polym. Sci. Polymer Chemistry Edition, vol. 20 pp. 233–239 (1982).
Physikalische und Chemische Aspeckte der Reversion, Kautschuk + Gummi–Kunststoffe, 34, No. 9, 1981.
"Influence of the type and concentration of crosslinking agent on the effectiveness of a combined system of bismaeimide and sulfur," Kauchuk i Rezina, No. 10, pp. 15–19, 1985.
"High Temperature curing of general–purpose rubbers with a curing system comprising a bismaleimide and sulphur," Prashehinkina, A. S. et al., *Kauchuk i Rezina*, No. 4, 1977, p. 21.
"Determination of Degree of Crosslinking in Natural Rubber Vulcanizates." Part III, L. Mullins, *Journ. of Appl. Poly. Sci.*, vol. II, issue No. 4, pp. 1–7, 1959.
"A Theory of Large Elastic Deformation," M. Mooney, *Journ. of Applied Physics*, vol. 2, Sep. 1940, pp. 582–592.
"Structural Characterization of Sulfur–Vulcanized Rubber Networks," B. Saville and A. A. Watson, Rubber Chemistry & Technology, 40, 100 (1967).
"Structural Characterization of Vulcanizates Part X. Thiol–Disul-fide Interchange for Cleaving Disulfide Crosslinks in Natural Rubberwr Vulcanizates," D. S. Campbell, Journal of Appl. Poly, Sci. vol. 13, pp. 1201–1214, 1969.
"Determination of Degree of Crosslinking in Natural Rubber Vulcanizates." Part II. C. G. Moore and W. F. Watson, Journ. of Polymer Sci., vol. XIX, pp. 237–254, 1956.
"Reaction of Methyl Iodide with Vulcanizates," Industrial and Engineering Chemistry, vol. 36, No. 1, pp. 20–28 (1944).
"Advances in natural rubber for tires:compounding for improved car", Baker, C. S. L. et al., Elastometrics, Jul., 1989.
"Relation between the friction and Visco–Properties of Rubber," Grosch, K. A., Nature, Mar. 2, 1963, pp. 858–859.
"Relevence of Elastic and Loss Moduli of Tyre Components to Tyre Energy Losses," Collins. J. M. et al., Transactions of the Icstitution of the Rubber Industry, vol. 40, No. 6, Dec., 1964 pp. 239–256.

(List continued on next page.)

*Primary Examiner*—Edward J. Cain
*Attorney, Agent, or Firm*—Ralph J. Mancini; Louis A. Morris

[57] ABSTRACT

A rubber composition which is the vulcanization reaction product of a rubber, sulfur or a sulfur donor and particular anti-reversion coagents, is disclosed. The anti-reversion coagents only partially react under sulfur-vulcanization reaction conditions up to optimum cure, and, after optimum cure, form cross-links bonded to the sulfur cross-linked rubbers by carbon-carbon linkages. Also disclosed are a vulcanization process carried out in the presence of the anti-reversion coagents and the use of these anti-reversion coagents in the sulfur-vulcanization of rubbers. The anti-reversion coagents of the disclosure provide sulfur-vulcanized rubbers having significantly improved physical properties.

14 Claims, No Drawings

OTHER PUBLICATIONS

"Esters of Boric Acid Offering a Greater Flexibility for Cobalt Bonding Systems," Pieroth, M. and Schubart; L., Kautschuk Gummi, May 1990, pp. 385–387.

"Latest Developments in the Urethane Crosslinking of Natural Rubber," Baker, C. S. L., Kautschuk, Gummi, Aug. 1983, pp. 677–684.

"Vulcanisation of Highly Unsaturated Rubbers with N. N. B. I. S.—maleimide and Derivatives in Absence of Sulphur," Dominoin Rubber Co. Ltd., Can. 738,500, clg. 7. 5.59 (USA) as 811, 517, Pub. Dec. 7, 1966.

"Rubber Technology Handbook," Hofmann, Werner, Hanser Publishers, distrib. in U. S. by Oxford U. Press, pp. 424–429 (1989).

"Synthesis of N–Subsituted Bisitaconimide Monomers for Use as Thermosetting Polyimide Resins," Hartford, S. L. et al., Journ. of Poly. Sci., vol. 16, pp. 137–153 (1982).

Patent Abstracts of Japan, vol. 12, No. 462 (1988).

Patent Abstracts of Japan, vol. 13, No. 111 (1989).

International Search Report.

ANTI-REVERSION COAGENTS FOR RUBBER VULCANIZATION

This is a continuation of application Ser. No. 08/050,049, filed as PCT/EP91/02048, on Oct. 29, 1991, published as WO92/07904, on May 14, 1992 now U.S. Pat. No. 5,426,155.

This invention relates to a rubber composition having improved physical properties. More particularly, it relates to a sulfur-vulcanized rubber composition which is vulcanized in the presence of particular anti-reversion coagents. The invention also relates to a sulfur-vulcanization process which is carried out in the presence of particular anti-reversion coagents and the use of particular anti-reversion coagents in the sulfur-vulcanization of rubber. Finally, the invention also relates to rubber products comprising rubber vulcanized with sulfur in the presence of particular anti-reversion coagents.

In the tire and belt industries, among others, better mechanical and heat resistance properties are being demanded. It has long been known that the mechanical properties of rubber can be improved by using a large amount of sulfur as a cross-linking agent to increase the cross-link density in vulcanized rubbers. However, the use of large amounts of sulfur suffers from the disadvantage that it produces reversion and leads to a marked decrease in heat resistance and resistance to flex cracking, among other properties, in the final product. The fact that reversion is a continuing problem can be seen from, "Rubber Microstructure and Reversion," Nordsiek, Dr. K. H., *Rubber World*, 197 (3), pp. 30–38, 1987, and, "Physikalische und Chemische Aspekte der Reversion," *Kautschuk+Gummi–Kunstoffe* 34, No. 9, 1981.

In order to eliminate the foregoing disadvantage, it has been proposed to add coagents to sulfur-vulcanization systems. One known type of coagent are the maleimides. Such vulcanization systems are disclosed in, "Vulcanization With Maleimides," *Journal of Applied Polymer Science*, Vol. 8, pp. 2281–2298 (1964).

U.S. Pat. No. 3,297,713 suggests the use of dithiobis (N-phenylmaleimides) as vulcanizing agents for rubber. However, this system does not employ sulfur as a vulcanization agent and thus suffers from several disadvantages which result from the absence of sulfur cross-links in the rubber product.

Japanese patent publication J6 1014-238 discloses sulfur-vulcanization systems wherein maleimides are used as coagents and which also contain either dibenzothiazyl disulfide or tetramethylthiuram disulfide. However, this solution is of limited application since only vulcanization accelerators having relatively short scorch times can be used with the bis-maleimides.

European patent application 0 191 931 suggests that the use of a bis-maleimide compound in combination with a sulfenamide and a dithiophosphoric acid leads to further improvements in the mechanical and anti-reversion properties of sulfur-vulcanized rubbers. The patent specification claims that these rubbers exhibit improved resistance to reversion, resistance to heat ageing and resistance to flex cracking. However, this system is limited to vulcanization carried out in the presence of a sulfenamide accelerator in combination with a dithiophosphoric acid accelerator and is thus of limited utility in actual practice.

In the article, "Change in the Structure and Properties of Vulcanizates Based on Natural Rubber Under Prolonged Vulcanization in the Presence of Vulcanizing Systems Containing Sulfur and Bismaleimides," Chavchich, T. A., et al., *Kauchuk i Rezina*, vol. 4, pp. 20–3, 1981, there is disclosed that vulcanization of natural rubber tread stocks with sulfur in the presence of m-phenylenebis-maleimide at 143° C. over a 600-minute period gave vulcanizates with enhanced physiomechanical properties and resistance to reversion.

Other articles relating to the sulfur-vulcanization of rubbers using bismaleimides as coagents include, "Vulcanization of cis-1,4-isoprene rubber by derivatives of maleimide under the action of high temperatures and radiation," *Kauchuk i Rezina*, vol. 3, pp. 10–12, 1974; "High-temperature Vulcanization of Unsaturated Rubbers by Thio Derivatives of Maleimide," *Kauchuk i Rezina*, vol. 3, pp. 16–19, 1975; and, "Influence of the Type and Concentration of Crosslinking Agent on the Effectiveness of a Combined System of Bismaleimide and Sulfur," *Kauchuk i Rezina*, No. 10, pp. 15–19, 1985.

Even more recently, Japanese patent applications J6 3286-445 and J6 3312-333 disclosed the vulcanization of rubber with sulfur and an aliphatic bis-maleimide or N,N'-toluene bis-maleimide. These particular bis-maleimides are said to improve the heat resistance and adhesion properties of the rubbers.

Further, European patent applications 345 825 and 410 152 also relate to the use of bismaleimides as coagents in sulfur-vulcanization of rubber. These two patents are directed to vulcanization systems which contain a second coagent, presumably to improve upon the bismaleimide system.

However, despite the fact that some of the above patents claim to reduce reversion by addition of a bismaleimide, in actual practice the reduction in reversion achieved with the bismaleimides is insufficient. Accordingly, although the reversion and the heat resistance are slightly improved, the problem remains that there is no generally applicable anti-reversion agent which may be used in combination with a number of different rubber accelerators during the vulcanization process and which satisfactorily solves the reversion problem while at the same time significantly improving the heat resistance of sulfur-vulcanized rubbers without having an adverse affect on other rubber properties.

Another type of curing system used to inhibit reversion in rubbers is disclosed in, "Latest Developments in the Urethane Crosslinking of Natural Rubber," *Kautschuk+Gummi–Kunstoffe* 36, pp. 677–684, 1983. However, this so-called NOVOR system also suffers from several disadvantages including very limited applicability to particular vulcanization processes.

Further, in Canadian Patent no. 738,500 the vulcanization of rubbers in the absence of sulfur, with either bis-maleimides and bis-citraconimides, is disclosed. This process had, for its purpose, to be an alternative to sulfur-vulcanization processes. However, the rubber products made by the process of this patent suffer from the usual disadvantages of peroxide-cured rubbers such as low tensile strength and significant reductions in other important properties. This patent does not disclose the use of the bis-maleimides or bis-citraconimides in the sulfur-vulcanization of rubber.

The present invention provides a solution to the above problems by the use of a novel class of anti-reversion coagents in the sulfur-vulcanization of rubbers. More particularly, in a first aspect, the present invention relates to a sulfur-vulcanized rubber composition which comprises the vulcanization reaction product of:

(A) 100 parts by weight of at least one natural or synthetic rubber;

(B) 0.1 to 25 parts by weight of sulfur and/or a sufficient amount of a sulfur donor to provide the equivalent of 0.1 to 25 parts by weight of sulfur; and (C) 0.1 to 5.0 parts by weight of a coagent which only partially reacts under sulfur-vulcanization reaction conditions up to optimum cure, and which, after optimum cure, forms cross-links bonded to the sulfur cross-linked rubber by a carbon-carbon linkage at a rate sufficient to compensate for from 10 to 200 percent of the reversion in said rubber composition.

In addition, the present invention relates to a vulcanization process carried out in the presence of the anti-reversion coagents and the use of these anti-reversion coagents in the sulfur-vulcanization of rubbers. Further, the invention also encompasses rubber products which comprise at least some rubber which has been vulcanized with sulfur in the presence of said anti-reversion coagents.

The present invention provides an excellent anti-reversion effect as well as improvements in several rubber properties without having a significant adverse effect on the remaining properties, when compared with similar sulfur-vulcanization systems using other coagents.

The present invention is applicable to all natural and synthetic rubbers. Examples of such rubbers include, but are not limited to, natural rubber, styrene-butadiene rubber, butadiene rubber, isoprene rubber, acrylonitrile-butadiene rubber, chloroprene rubber, isoprene-isobutylene rubber, brominated isoprene-isobutylene rubber, chlorinated isoprene-isobutylene rubber, ethylene-propylene-diene terpolymers, as well as combinations of two or more of these rubbers and combinations of one or more of these rubbers with other rubbers and/or thermoplastics.

Examples of sulfur which may be used in the present invention include various types of sulfur such as powdered sulfur, precipitated sulfur and insoluble sulfur. Also, sulfur donors may be used in place of, or in addition to sulfur in order to provide the required level of sulfur during the vulcanization process. Examples of such sulfur donors include, but are not limited to, tetramethylthiuram disulfide, tetraethylthiuram disulfide, tetrabutylthiuram disulfide, dipentamethylene thiuram hexasulfide, dipentamethylene thiuram tetrasulfide, dithiodimorpholine and mixtures thereof.

In this text, references to sulfur shall include sulfur donors and mixtures of sulfur and sulfur donors. Further, references to the quantity of sulfur employed in the vulcanization, when applied to sulfur donors, refer to a quantity of sulfur donor which is required to provide the equivalent amount of sulfur that is specified.

The anti-reversion coagents of the present invention are characterized by the fact that they must be capable of forming cross-links bonded to the rubber by a carbon-carbon linkage. This type of cross-link is known in the rubber literature from, for example, "High-temperature vulcanization of unsaturated rubbers by thio derivatives of maleimide," Krashennikov et al., *Kauchuk i Rezina,* No. 3, pp. 16–20, 1975. Such cross-links bonded to the rubber by a carbon-carbon linkage are highly desirable in rubbers, and particularly sulfur-vulcanized rubbers since such cross-links are thermally stable.

Accordingly, we have found that it is desirable, in sulfur-vulcanization, to produce cross-links bonded to the rubber by carbon-carbon linkages. For the purposes of this patent application, these cross-links will be hereinafter referred to as, "carbon-carbon" cross-links. In order to make a thermally stable rubber composition which still possesses the advantageous properties of sulfur-vulcanization, however, it remains necessary to combine the formation of carbon-carbon linkages with the formation of the stable monosulfidic cross-links which result from sulfur-vulcanization.

While it is possible to obtain a significant number of carbon-carbon cross-links by sulfur-vulcanizing rubber in the presence of bismaleimides, we have found that such rubbers still suffer from significant reversion (reduction in the cross-link density) upon thermal loading of the rubber after vulcanization. This leads to a corresponding decrease in some of the important properties of such rubber compositions during their use in, for example, tires.

While not wishing to be bound by any particular theory, it is thought that the anti-reversion coagents of the present invention solve this long-standing problem since they are sufficiently unreactive under sulfur-vulcanization conditions such that, at optimum cure, a substantial portion of the coagent remains in the rubber composition in a form in which it is still capable of reacting with the sulfur-vulcanized rubber to form additional cross-links, which cross-links are bonded to the rubber by a carbon-carbon linkage.

One possible measure of the reactivity of the anti-reversion coagents under sulfur-vulcanization conditions up to optimum cure is cross-linking efficiency. Cross-linking efficiency, in the context of this patent application, refers to a measure of the percentage increase or decrease in shear modulus of the vulcanized rubber, per millimole of anti-reversion coagent, per 100 grams of rubber, as compared with the same rubber composition vulcanized under the same reaction conditions in the absence of the anti-reversion coagent. The shear modulus measurements for determining the cross-linking efficiency are made on a rubber composition at optimum cure. For a definition of optimum cure see, W. Hofmann, "Rubber Technology Handbook."

For example, if 1 millimole of anti-reversion coagent, when compared to the $t_{90}$ control, gives an increase in the shear modulus (as measured in accordance with the procedure of the examples hereafter) of 0.5% at optimum cure, then the cross-linking efficiency for that anti-reversion coagent is 0.5%. With $t_{90}$ control is meant the optimum cure time of a rubber composition vulcanized without anti-reversion coagent. In addition, if for the same amount of coagent, 0.3% less crosslinks are formed, then the cross-linking efficiency is −0.3%.

The cross-linking efficiency gives an indication of the influence of the coagent on the sulfur-vulcanization up to optimum cure and thereby an indication of the cross-linking reactivity of the coagent under sulfur-vulcanization conditions. In general, the anti-reversion coagents of the present invention exert little influence on the sulfur-vulcanized rubber up to optimum cure.

We have found that the preferred anti-reversion coagents of the present invention generally exhibit a cross-linking efficiency of between 2.0 and −2.0%. More preferred coagents have a cross-linking efficiency of 1.0 to −1.0%, and most preferred coagents have a cross-linking efficiency of 0.5 to −0.5%. However, it should be noted that the cross-linking efficiency is only an inidication of the reactivity of the coagent up to optimum cure, and does not directly measure what is thought to be the important feature of the coagents of the present invention, namely that some of the coagent is still present at optimum cure in a form capable of reacting with the sulfur-vulcanized rubber to form additional cross-links. Thus, some useful coagents may have a higher or lower cross-linking efficiency but still fall within the scope of the present invention if they meet all of the other criteria.

The final characterizing feature of the coagents of the present invention is that they must form stable carbon-carbon cross-links at a rate sufficient to compensate for 10–200% of the reversion in that rubber composition. It is this final feature of the present coagents which prevents significant reversion of the sulfur-vulcanized rubber since, the degraded polysulfide cross-links are simply replaced by the thermally stable carbon-carbon cross-links formed by the anti-reversion coagents, thereby holding the torque at a relatively constant level.

The rate of formation of carbon-carbon cross-links after optimum cure can vary within a particular range depending upon how much reversion or marching can be tolerated in the particular rubber composition. Marching is when the compensation of the coagent exceeds the reversion such that, after optimum cure, a further increase in the cross-link density occurs. It is preferred that the coagent exhibit a reactivity which compensates for at least 10% of the reversion in the rubber composition and not more than 200%, of the reversion. More preferably, the coagent compensates for from 40–150% of the reversion and most preferably for 70–120% of the reversion. Of course, the amount of anti-reversion compensation which is desired and/or acceptable depends to a great extent on the particular rubber composition, the application in which the rubber is used and the conditions to which the rubber will be exposed during its lifetime.

Anti-reversion coagents of the present invention include, but are not limited to compounds represented by the general formula A:

$$Q_1 - D - (Q_2)_n \qquad (A);$$

wherein D, optionally containing one or more heteroatoms or groups selected from nitrogen, oxygen, silicon, phosphorus, boron, sulphone and sulphoxy, is a monomeric or oligomeric divalent, trivalent or tetravalent group, n is an integer selected from 1, 2 or 3, $Q_1$ and $Q_2$ are independently selected from the formulas I and II:

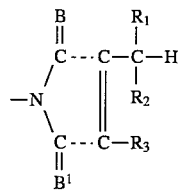

and;

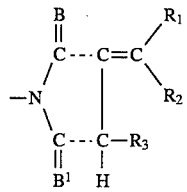

wherein $R_1$, $R_2$ and $R_3$ are independently selected from hydrogen, $C_1$–$C_{18}$ alkyl groups, $C_3$–$C_{18}$ cycloalkyl groups, $C_6$–$C_{18}$ aryl groups, $C_7$–$C_{30}$ aralkyl groups and $C_7$–$C_{30}$ alkaryl groups and $R_2$ and $R_3$ may combine to form a ring when $R_1$ is hydrogen; B and $B^1$ are independently selected from the following hetero atoms: oxygen and sulfur.

The imides of the present invention are, in general, known compounds and may be prepared by the methods disclosed in, "The synthesis of Biscitraconimides and Polybiscitraconimides," Galanti, A. V. and Scola, D. A., Journ. of Poly. Sci.: Polymer Chemistry Edition, Vol. 19, pp. 451–475, (1981); and "The Synthesis of Bisitaconamic Acids, Isomeric Bisimide Monomers," Galanti, A. V. et al., Journ. Poly. Sci.: Polymer Chemistry Edition, Vol. 20, pp. 233–239 (1982) and Hartford, S. L., Subramanian, S. and Parker, J. A., Journ. Poly. Sci.: Polymer Chemistry Edition, Vol. 16, p. 137, 1982, the disclosures of which are hereby incorporated by reference.

The imide compounds useful in the present invention and represented by the formula A include, but are not limited to, the biscitraconimides wherein $Q_1$ and $Q_2$ are of the formula I, $R_1=R_2=R_3=H$, n=1 and $B=B^1$=oxygen the bis-itaconimides wherein $Q_1$ and $Q_2$ are of the formula II, $R_1=R_2=R_3=H$, n=1 and $B=B^1$=oxygen; the mixed citraconimide and itaconimide wherein $Q_1$ is of the formula I, $Q_2$ is of the formula II, $R_1=R_2=R_3=H$, n=1 and $B=B^1$= oxygen; and mixtures of the above-mentioned compounds.

More specifically, the group D mentioned in the formula A can be a monomeric divalent, trivalent or tetravalent linear or branched radical chosen from a $C_1$–$C_{18}$ alkyl, $C_2$–$C_{18}$ alkenyl, $C_2$–$C_{18}$ alkynyl, $C_3$–$C_{18}$ cycloalkyl, $C_3$–$C_{18}$ polycycloalkyl, $C_6$–$C_{18}$ aryl, $C_6$–$C_{30}$ polyaryl, $C_7$–$C_{30}$ aralkyl, $C_7$–$C_{30}$ alkaryl, oligomers of one or more of these radicals, and which radicals may optionally contain one or more of oxygen, nitrogen, silicon, phosphorus, sulphone, sulfoxy and boron, all of which radicals may also be optionally substituted at one or more of the atoms in the radical with a substituent selected from oxygen, nitrogen, silicon, $SiO_2$, sulfoxy, boron, phosphorus, amido, imino, azo, diazo, hydrazo, azoxy, alkoxy, hydroxy, iodine, fluorine, bromine, chlorine, carbonyl, carboxy, ester, carboxylate, $SO_2$, $SO_3$, sulphonamido, $SiO_3$, nitro, imido, thiocarbonyl, cyano, and epoxy groups.

More specific examples of some of the imide compounds useful in the present invention include, but are not limited to, the following:

N,N'-ethylene-bis-citraconic imide (BCI-C2);
N,N'-hexamethylene-bis-citraconic imide (BCI-C6);
N,N'-tetramethylene-bis-citraconic imide;
N,N'-2-methyl-pentamethylene-bis-citraconic imide;
N,N'-(1,3-propylene)-bis-citraconic imide;
N,N'-(3,3'-oxydipropylene)-bis-citraconic imide;
N,N'-(aminodiethylene)-bis-citraconic imide;
N,N'-(aminodipropylene)-bis-citraconic imide;
N,N'-(1,10-(4,7-dioxa)-decanediyl)-bis-citraconic imide;
N,N'- (4,4'-(di-(2-methylcyclohexyl)methylene)-bis-citraconic imide;
N,N'-(4,4'-dicyclohexyl-isopropylene)bis-citraconic imide;
N,N'-(4,4'-dicyclohexyloxy)-bis-citraconic imide;
N,N'-(4,4'-dicyclohexylene)-bis-citraconic imide;
N,N'-o-phenylene-bis-citraconic imide; N,N'-m-phenylene-bis-citraconic imide(BCI-MP); N,N'-m-phenylene-bis-itacontc imide (BII-MP);
N,N'-p-phenylene-bis-citraconic imide;
N,N'-(5-chloro-1,3-phenylene)-bis-citraconic imide;
N,N'-(5-hydroxy-1,3-phenylene)-bis-citraconic imide;
N,N'-(5-methoxy-1,3-phenylene)-bis-citraconic imide;
N,N'-($\alpha,\alpha$'-(1,3-dimethyl phenylene))-bis-citraconic imide;
N,N'-(4,4'-(1,10-decanediol-dibenzoate))-bis-citraconic imide (BCI-BAE10); N,N'-(4,4'-diphenyl-bisphenol-A-ether)-bis-citraconic imide; N,N'-(4,4'-biphenylene)-bis-citraconic imide;
N,N'-(4,4'-diphenylmethylene)-bis-citraconic imide (BCI-DPM);
N,N'-(4,4'-diphenylmethylene)-bis-itaconic imide (BII-DPM);
N,N'-m-xylylene-bis-citraconic imide (BCI-MX);
N,N'-(4,4'-diphenylisopropylene)-bis-citraconic imide;
N,N'-(3,3'-dimethyl-4,4'-biphenylene)-bis-citraconic imide;
N,N'-(3,3'-dichloro-4,4'-biphenylene-bis-citraconic imide;
N,N'-(3,3'-difluoro-4,4'-biphenylene)-bis-citraconic imide;
N,N'-(4,4'-oxydiphenylene)-bis-citraconic imide;
N,N'-(4,4'-diphenylsulfone)-bis-citraconic imide;
N,N'-(4,4'-diphenylcarboxy)-bis-citraconic imide;
N,N'-(4,4'-(1,1-diphenylpropylene))-bis-citraconic imide;

N,N'-3,5-(1,2,4-triazole)-bis-citraconic imide;
N,N'-dodecamethylene-bis-citraconic imide;
N,N'-(2,2,4-trimethylhexamethylene)-bis-citraconic imide;
N,N'-(1,11-(4,8-dioxa-undecanediyl))-bis-citraconic imide;
N,N'-(4,4'-benzophenonediyl)-bis-citraconic imide;
N,N'-(1,4-anthraquinonediyl)-bis-citraconic imide;
N,N'-(1,3-naphthalenediyl)-bis-citraconic imide;
N,N'-(1,4-naphthalenediyl)-bis-citraconic imide;
N,N'-(1,5-naphthalenediyl)-bis-citraconic imide;
N,N'-(1,3-cyclohexylene)-bis-citraconic imide;
N,N'-(1,4-cyclohexylene)-bis-citraconic imide;
N,N'-(5-methyl-1,3-phenylene)-bis-citraconic imide;
N,N'-($\alpha,\alpha$'-(1,3-dimethylcyclohexylene))-bis-citraconic imide (BCI-BAC);
N,N'-($\alpha$,3-(1,1,5,5-tetramethyl-cyclohexylene))-bis-citraconic imide;
N,N'-(isophoronyl)-bis-citraconic imide;
N,N'-(dimethyltricyclododecylene)-bis-citraconic imide;
N,N'-octamethylene-bis-citraconic imide;
N,N'-(1,2-propylene)-bis-citraconic imide;
N,N'-decamethylene-bis-citraconic imide;
N,N'-heptamethylene-bis-citraconic imide;
N,N'-(5-bromo-1,3-phenylene)-bis-citraconic imide;
N,N'-(1,13-(7-aza-tridecanediyl))-bis-citraconic imide;
N,N'-(1,7-(4-aza-heptanediyl))-bis-citraconic imide;
N,N'-(1,11-(3,6,9-triaza-undecanediyl))-bis-citraconic imide;
N,N'-(1,8-(3,6-diaza-octanediyl)-bis-citraconic imide;
N,N'-(N,N'-di-2-ethylpiperazinyl)-bis-citraconic imide;
N,N'-(2-hydroxy-1,3-propylene)-bis-citraconic imide;
N,N',N"-(2,4,6-trihexamethylene-isocyanuratetriyl)-tris-citraconic imide (TCI-AA33); N,N'-(3,5-benzoic aciddiyl)-bis-citraconic imide;
N,N'-pentamethylene-bis-citraconic imide;
N,N'-undecamethylene-bis-citraconic imide;
N,N'-(4-(N-methylene-citraconic imide)-octamethylene-bis-citraconic imide (TCI-C9v); N,N'-nonamethylene-bis-citraconic imide;
N,N'-(2-butyl-2-ethylpentamethylene)-bis-citraconic imide;
N,N'-polytetrahydrofuryl-bis-citraconic imide; N,N'-(Jeffamine D230®)-bis-citraconic imide; N,N'-(Jeffamine D2000®)-bis-citraconic imide; and N,N'-(Jeffamine ED600®)-bis-citraconic imide.

Jeffamine D230®, Jeffamine D2000® and Jeffamine ED600® are registered tradenames of the Texaco company. The biscitraconic imides based on these amines have the following general structure:

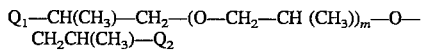

$Q_1$ and $Q_2$ are as defined above. m represents from 1 up to 1000.

In addition, the bis-, tris- and tetra-itaconimides of the present invention may be the same as mentioned above, except that all citraconimide groups are exchanged for itaconimide groups. The same materials as mentioned above may be mixed imides if some of the citraconimide groups are exchanged for itaconimide groups.

The amount of sulfur to be compounded with the rubber is, based on 100 parts of rubber, usually 0.1 to 25 parts by weight, and more preferably 0.2 to 8 parts by weight. The amount of sulfur donor to be compounded with the rubber is an amount sufficient to provide an equivalent amount of sulfur which is the same as if sulfur itself were used.

The amount of anti-reversion coagent to be compounded with the rubber is, based on 100 parts of rubber, 0.1 to 5 parts by weight, and more preferably 0.2 to 3.0 parts by weight.

These ingredients may be employed as a pre-mix, or added simultaneously or separately, and they may be added together with other rubber compounding ingredients as well.

In most circumstances it is also desirable to have a vulcanization accelerator in the rubber compound. Conventional, known vulcanization accelerators may be employed. The preferred vulcanization accelerators include mercaptobenzothiazole, 2,2'-mercaptobenzothiazole disulfide, sulfenamide accelerators including
N-cyclohexyl-2-benzothiazole sulfenamide,
N-tertiary-butyl-2-benzothiazole sulfenamide,
N,N'-dicyclohexyl-2-benzothiazole sulfenamide, and
2-(morpholinothio)benzothiazole; thiophosphoric acid derivative accelerators, thiurams, dithiocarbamates, diphenyl guanidine, diorthotolyl guanidine, dithiocarbamylsulfenamides, xanthates, triazine accelerators and mixtures thereof.

When the vulcanization accelerator is employed, quantities of from 0.1 to 8 parts by weight, based on 100 parts by weight of rubber composition, are used. More preferably, the vulcanization accelerator comprises 0.3 to 4.0 parts by weight, based on 100 parts by weight of rubber.

Other conventional rubber additives may also be employed in their usual amounts. For example, reinforcing agent such as carbon black, silica, clay, whiting and other mineral fillers, as well as mixtures of fillers, may be included in the rubber composition. Other additives such as process oils, tackifiers, waxes, antioxidants, antiozonants, pigments, resins, plasticizers, process aids, factice, compounding agents and activators such as stearic acid and zinc oxide may be included in conventional, known amounts. For a more complete listing of rubber additives which may be used in combination with the present invention see, W. Hofmann, "Rubber Technology Handbook, Chapter 4, Rubber Chemicals and Additives, pp. 217–353, Hanser Publishers, Munich 1989.

Further, scorch retarders such as phthalic anhydride, pyromellitic anhydride, benzene hexacarboxylic trianhydride, 4-methylphthalic anhydride, trimellitic anhydride, 4-chlorophthalic anhydride, N-cyclohexyl-thiophthalimide, salicylic acid, benzoic acid, maleic anhydride and N-nitrosodiphenylamine may also be included in the rubber composition in conventional, known amounts. Finally, in specific applications it may also be desirable to include steel-cord adhesion promoters such as cobalt salts and dithiosulfates in conventional, known quantities.

The present invention also relates to a vulcanization process which comprises the step of vulcanizing at least one natural or synthetic rubber in the presence of 0.1 to 25 parts by weight of sulfur or a sulfur donor per 100 parts by weight of rubber, characterized in that said process is carried out in the presence of an effective amount of a coagent which only partially reacts under sulfur-vulcanization reaction conditions up to optimum cure, and which, after optimum cure, forms cross-links bonded to the sulfur cross-linked rubber by a carbon-carbon linkage at a rate sufficient to compensate for from 10 to 200 percent of the reversion in said rubber composition.

The process is carried out at a temperature of 110°–220° C. over a period of up to 24 hours. More preferably, the process is carried out at a temperature of 120°–190° C. over a period of up to 8 hours in the presence of 0.1 to 5.0 parts by weight of anti-reversion coagent. Even more preferable is the use of 0.2–3.0 parts by weight of anti-reversion coagent. All of the additives mentioned above with respect to the rubber composition may also be present during the vulcanization process of the invention.

In a more preferred embodiment of the vulcanization process, the vulcanization is carried out at a temperature of 120°–190° C. over a period of up to 8 hours and in the presence of 0.1 to 8.0 parts by weight, based on 100 parts by weight of rubber, of at least one vulcanization accelerator.

In another preferred embodiment of the vulcanization process, the anti-reversion coagent is selected from a compound of the formula A.

The present invention also comprises the use of an anti-reversion coagent which only partially reacts under sulfur-vulcanization reaction conditions up to optimum cure, and which, after optimum cure, forms cross-links bonded to the sulfur cross-linked rubber by a carbon-carbon linkage at a rate sufficient to compensate for from 10 to 200 percent of the reversion in said rubber composition, in a process for the sulfur-vulcanization of rubber.

Finally, the present invention also includes articles of manufacture, such as tires, which comprise sulfur-vulcanized rubber which is vulcanized in the presence of the anti-reversion coagents of the present invention.

The invention is further illustrated by the following examples which are not to be construed as limiting the invention in any way. The scope of the invention is to be determined from the claims appended hereto.

EXPERIMENTAL METHODS USED IN THE EXAMPLES

Structural Characterization of the Rubber Network

The crosslink density and the distribution of poly-, di- and monosulfidic and non-sulfidic crosslinks has been determined in a rubber compound based on a natural rubber (NR) gum recipe (NR SMR CV5 100 parts, stearic acid 2 phr, ZnO RS 5 phr, Perkacit® CBS 0.6 phr, sulfur 2.3 phr), all amounts being related to the amount of rubber, which recipe was mixed on a two-roll mill and vulcanized as described below.

The density of crosslinks was determined from the elastic constant (J. Mullins, J. Appl. Polym. Sci. 2, 1, 1959; J. Mooney et al., J. Appl. Physics, 11, 100, 1940) following the procedure given by Saville and Watson (Rubber Chem. Technol. 40, 100, 1967). The proportions of the sulfidic crosslinks were determined by thiol-amine chemical probes (D. S. Campbell et al., J. Appl. Polym. Sci. 13, 1201, 1969 and Proc. Int. Conf. 5th, 1, 1967, 1968), and the proportions of non-sulfidic, carbon-carbon, crosslinks by methyl iodide treatment (C. G. Moore et al., J. Polym. Sci. 19, 237, 1956 and 32, 503, 1958; M. L. Selker et al., Ind. Eng. Chem. 36, 20, 1944).

Compounding, Vulcanization and Characterization of Compounds

In the following examples, rubber compounding, vulcanization and testing was carried out according to standard methods except as otherwise stated:

Base compounds were mixed in a Farrel Bridge BR 1.6 liter Banbury type internal mixer (preheating at 50° C., rotor speed 77 rpm, mixing time 6 min with full cooling).

Vulcanization ingredients and coagents were addded to the compounds on a Schwabenthan Polymix 150L two-roll mill (friction 1:1.22, temperature 70° C., 3min).

Mooney viscosity was determined using a Mooney viscosimeter MV 2000E at 100° C. according to ASTM D1646-89.

Scorch times were determined using a Mooney viscosimeter MV 2000E at 121° C. as time to until an increase of 5 Mooney units was observed (t+5; ASTM D 1646-89).

Cure characteristics were determined using a Goettfert elastograph or Monsanto rheometer ODR (arc 1°) or MDR 2000E (arc 0.5°): delta torque or extent of crosslinking (R∞) is the maximum torque (MH, also denoted as initial torque maximum, $T_i$) minus the minimum torque (ML). Scorch safety ($t_s2$) is the time to 2%, of delta torque above minimum torque (ML), optimum cure time ($t_{90}$) is the time to 90% of delta torque above minimum, reversion time ($t_r2$) is the time to 2%, of delta torque below maximum torque. Final torque ($T_f$) is the torque measured after the overcure time.

Sheets and test specimens were vulcanized by compression molding in a Fontyne TP-400 press.

Tensile measurements were carried out using a Zwick 1445 tensile tester (ISO-2 dumbbells, tensile properties according to ASTM D 412-87, tear strength according to ASTM D 624-86).

Hardness was determined according to DIN 53505, and ISO 48 (IRHD).

Rebound resilience was measured at room temperature (RT) or at 100° C. according to ASTM D 1054-87.

Compression set was determined after 24 h at 70° C. or 72 h at 23° C. according to ASTM D 395-89.

Heat build-up and compression set after dynamic loading were determined using a Goodrich Flexometer (load 1 MPa, stroke 0.445 cm, frequency 30 Hz, start temperature 100° C., running time 30 min or till blow out; ASTM D 623-78).

Fatigue to failure was determined using a Monsanto FTFT tester (cam 24; ASTM D 4482).

Abrasion was determined using a Zwick abrasion tester as volume loss per 40 m path travelled (DIN 53516).

Dynamic mechanical analysis was carried out using an Eplexor Dynamic Mechanical Analyzer (prestrain 10%, frequency 15 Hz, ASTM D 2231)

EXAMPLES 1–5 AND COMPARATIVE EXAMPLES A AND B

Five different imide anti-reversion agents in accordance with the present invention were prepared and tested in the sulfur vulcanization process according to the present invention. The imides employed were the following:

1. N,N'-m-phenylene-bis-citraconic imide (BCI-MP);
2. N,N'-ethylene-bis-citraconic imide (BCI-C2);
3. N,N'-hexamethylene-bis-citraconic imide (BCI-C6);
4. N,N'-1,3-dimethyl-cyclohexyl-bis-citraconic imide (BCI-BAC);
5. N,N'-m-xylylene-bis-citraconic imide (BCI-MX); and
A. N,N'-m-phenylene-bis-maleimide (HVA-2®) (ex. Du Pont);

The accelerator employed was n-cyclohexyl-2-benzothiazole sulfenamide (CBS). Comparative example B was a control example with no anti-reversion additive. Natural rubber was vulcanized in the presence of the foregoing compounds using the formulations listed in Table 1.

TABLE 1

| Example No. | 1 | 2 | 3 | 4 | 5 | A | B |
|---|---|---|---|---|---|---|---|
| Compound | | | | | | | |
| Natural Rubber | 100 | 100 | 100 | 100 | 100 | 100 | 100 |
| Carbon Black | 50 | 50 | 50 | 50 | 50 | 50 | 50 |
| Zinc Oxide | 5 | 5 | 5 | 5 | 5 | 5 | 5 |
| Stearic Acid | 2 | 2 | 2 | 2 | 2 | 2 | 2 |
| CBS | 1 | 1 | 1 | 1 | 1 | 1 | 1 |
| Sulfur | 2.3 | 2.3 | 2.3 | 2.3 | 2.3 | 2.3 | 2.3 |
| BCI-MP | 1.5 | — | — | — | — | — | — |
| BCI-C2 | — | 1.2 | — | — | — | — | — |
| BCI-C6 | — | — | 1.5 | — | — | — | — |

TABLE 1-continued

| Example No. | 1 | 2 | 3 | 4 | 5 | A | B |
|---|---|---|---|---|---|---|---|
| BCI-BAC | — | — | — | 1.6 | — | — | — |
| BCI-MX | — | — | — | — | 1.6 | — | — |
| HVA-2 ® | — | — | — | — | — | 1.3 | — |

The vulcanized rubbers listed in Table 1 were then tested for anti-reversion and other physical properties upon over-cure. The results are given in Table 2.

TABLE 2

Evaluation of bis-citraconimides for improvement of mechanical properties relative to bis-maleimide upon (over)cure at 180° C. for 60 minutes.

| Example No. | 1 | 2 | 3 | 4 | 5 | A | B |
|---|---|---|---|---|---|---|---|
| Mechanical property | | | | | | | |
| Hardness (Sh A) | 70 | 68 | 69 | 68 | 69 | 67 | 62 |
| Modulus 300% (MPa) | 13.3 | 13.2 | 13.8 | 18.4 | 19.4 | 10.5 | 9.0 |
| Tensile strength (MPa) | 17.4 | 19.8 | 23.0 | 21.4 | 21.4 | 18.3 | 17.4 |
| Compression set | 9.8 | 8.0 | 8.9 | — | — | 12.1 | 11.0 |
| Reversion (%)* | −3 | −2 | −13 | −4 | −6 | 22 | 30 |

$$*\text{Reversion} = \frac{[\text{Mod.300\%, at 180° C., } t_{90}] - [\text{Mod.300\%, at 180° C. 60 min.}]}{[\text{Mod.300\%, at 150° C., } t_{90}]} \times 100$$

— = not tested

These results show that with the known bis-maleimide anti-reversion agent a reduced reversion was observed (22%). No reversion is represented by 0%. All of the anti-reversion agents of the present invention were significantly superior to the bis-maleimide, as can be seen from the observed physical properties wherein the bis-citraconimides gave higher 300% modulus values than the bis-maleimide. The agents of the present invention gave satisfactory properties due to their anti-reversion effect.

EXAMPLE 6 AND COMPARATIVE EXAMPLES C–F

The effects of several materials on the vulcanization curve of natural rubber vulcanized at 180° C. were determined. In addition to HVA-2® and BCI-MP, the following materials were employed:
D. Phenyl-maleimide (PMI) (ex. Janssen Chimica); and
E. Phenyl-citraconimide (PCI).

The accelerators employed were 2,2'-mercaptobenzothiazole disulfide (MBTS). Comparative example F was a control example with no anti-reversion additive. The rubber formulations which were employed are given in Table 3.

TABLE 3

| Example | 6 | C | D | E | F |
|---|---|---|---|---|---|
| Compound | | | | | |
| Natural Rubber | 100 | 100 | 100 | 100 | 100 |
| Carbon Black | 50 | 50 | 50 | 50 | 50 |
| Zinc Oxide | 5 | 5 | 5 | 5 | 5 |
| Stearic Acid | 2 | 2 | 2 | 2 | 2 |
| MBTS | 1 | 1 | 1 | 1 | 1 |
| Sulfur | 2.25 | 2.25 | 2.25 | 2.25 | 2.25 |
| HVA-2 | — | 2.0 | — | — | — |
| PMI | — | — | 2.6 | — | — |
| PCI | — | — | — | 2.8 | — |

Vulcanization curves were measured with a Göttfert Elastograph at 180° C. for a period up to 60 minutes. The anti-reversion effect can be seen by comparing the final torque ($T_f$) with the initial torque maximum ($T_i$).

TABLE 4

| Torque (Nm) | $T_i$ | $T_f$ |
|---|---|---|
| Example | | |
| 6 | 0.96 | 1.13 |
| C | 1.14 | 0.89 |
| D | 0.90 | 0.72 |
| E | 0.82 | 0.38 |
| F | 0.88 | 0.55 |

As in the previous examples, the BCI-MP anti-reversion agent slightly over-compensated for the reversion thereby providing a rubber with satisfactory physical properties. The PCI enhanced the reversion effect on the control example. The HVA-2® increased the viscosity during the vulcanization more than the PMI did but neither of these agents compensated as much for the reversion effect as did the BCI-MP.

EXAMPLES 7–14 AND COMPARATIVE EXAMPLE G

In these examples four different accelerators were used in combination with the anti-reversion agents of the present invention in order to demonstrate that the anti-reversion effect is independent of the accelerator employed. The rubber formulations shown in table 4 were vulcanized in accordance with the present invention.

The accelerators employed for these tests included MBTS, CBS, N,N'-dicyclohexyl-2-benzothiazole sulfenamide (DCBS) and MBS.

TABLE 5

| Example | 7 | 8 | 9 | 10 | 11 | 12 | 13 | 14 |
|---|---|---|---|---|---|---|---|---|
| Compound | | | | | | | | |
| Natural Rubber | 100 | 100 | 100 | 100 | 100 | 100 | 100 | 100 |
| Carbon Black | 50 | 50 | 50 | 50 | 50 | 50 | 50 | 50 |
| Zinc Oxide | 5 | 5 | 5 | 5 | 5 | 5 | 5 | 5 |
| Stearic Acid | 2 | 2 | 2 | 2 | 2 | 2 | 2 | 2 |
| MBTS | 1 | — | — | — | 1 | — | — | — |
| CBS | — | 1 | — | — | — | 1 | — | — |
| MBS | — | — | 1 | — | — | — | 1 | — |
| DCBS | — | — | — | 1 | — | — | — | 1 |
| Sulfur | 2.3 | 2.3 | 2.3 | 2.3 | 2.3 | 2.3 | 2.3 | 2.3 |
| BCI-MP | 1.5 | 1.5 | 1.5 | 1.5 | — | — | — | — |
| BCI-C6 | — | — | — | — | 1.5 | 1.5 | 1.5 | 1.5 |

All of the formulations gave similar vulcanization curves with superior torque retention upon overcure as compared with the controls without BCI. Mathematical analysis of the vulcanization curves showed that the anti-reversion effect was not influenced by the type of vulcanization accelerator used.

EXAMPLES 15–17

These examples compare the effects of different concentrations of N,N'-hexamethylene-bis-citraconimide. The results of vulcanization with three different concentrations of anti-reversion agents are given in Table 6.

To obtain the results given in Table 6, vulcanization was carried out at 180° C. over a period of 60 minutes.

TABLE 6

| Example | 15 | 16 | 17 | G |
|---|---|---|---|---|
| Compound | | | | |
| Natural Rubber | 100 | 100 | 100 | 100 |
| Carbon Black | 50 | 50 | 50 | 50 |
| Zinc Oxide | 5 | 5 | 5 | 5 |
| Stearic Acid | 2 | 2 | 2 | 2 |
| CBS | 1 | 1 | 1 | 1 |
| Sulfur | 2.3 | 2.3 | 2.3 | 2.3 |
| BCI-C6 | 0.75 | 1.5 | 2.25 | — |
| Hardness (Shore A) | 63 | 65 | 67 | 58 |
| Modulus (MPa) | | | | |
| 100% | 3.3 | 3.8 | 4.5 | 2.1 |
| 300% | 15.9 | 18.6 | 20.5 | 10.7 |

These results demonstrate that at varying concentrations the composition of the present invention gave generally superior hardness and modulus at all concentrations.

EXAMPLES 18–20 AND COMPARATIVE EXAMPLES H AND I

These examples demonstrate that the rubbers in accordance with the present invention exhibit significantly better properties after ageing than prior art rubbers do. More particularly, the compositions shown in Table 7 were vulcanized under three different sets of vulcanization conditions, and then subjected to ageing for 48 hours at 100° C.

The results given in Table 7 were obtained from vulcanization at 150° C. for a period of 7–11 minutes. The results given in Table 8, in which similarly numbered and lettered examples employed the same quantities of all ingredients, were obtained from vulcanization at 180° C. for a period of 2 minutes, and the results given in Table 9 were obtained from vulcanization at 180° C. for a period of 60 minutes.

TABLE 7

| Example | H1 | I1 | 18a | 19a | 20a |
|---|---|---|---|---|---|
| Natural Rubber | 100 | 100 | 100 | 100 | 100 |
| Carbon Black | 50 | 50 | 50 | 50 | 50 |
| Zinc Oxide | 5 | 5 | 5 | 5 | 5 |
| Stearic Acid | 2 | 2 | 2 | 2 | 2 |
| CBS | 1 | 1 | 1 | 1 | 1 |
| Sulfur | 2.3 | 2.3 | 2.3 | 2.3 | 2.3 |
| HVA-2 ® | — | 1.3 | — | — | — |
| BCI-MP | — | — | 1.5 | — | — |
| BCI-C2 | — | — | — | 1.2 | — |
| BCI-C6 | — | — | — | — | 1.5 |
| Ageing Properties | | | | | |
| Hardness (Shore A) | 61 | 60 | 69 | 66 | 64 |
| Modulus (MPa) 100% | 3.5 | 3.2 | 4.2 | 3.7 | 3.7 |
| Tensile Strength (MPa) | 7.2 | 5.9 | 7.9 | 8.4 | 8.7 |

TABLE 8

| Example | H2 | I2 | 18b | 19b | 20b |
|---|---|---|---|---|---|
| Ageing Properties | | | | | |
| Hardness (Shore A) | 62 | 62 | 66 | 65 | 64 |
| Modulus (MPa) 100% | 3.4 | 3.4 | 4.3 | 3.9 | 3.8 |
| Tensile Strength (MPa) | 6.6 | 6.4 | 7.7 | 8.3 | 7.0 |

TABLE 9

| Example | H3 | I3 | 18c | 19c | 20c |
|---|---|---|---|---|---|
| Ageing Properties | | | | | |
| Hardness (Shore A) | 52 | 60 | 63 | 59 | 63 |
| Modulus (MPa) 100% | 2.3 | 2.4 | 3.0 | 3.1 | 3.0 |
| Tensile Strength (MPa) | 6.4 | 6.7 | 8.1 | 9.3 | 8.7 |

These results show that, in general, the rubbers of the present invention exhibit superior properties after ageing as compared with comparable prior art rubber compositions.

EXAMPLES 21–22 AND COMPARATIVE EXAMPLE J

The effect of two anti-reversion agents of the present invention was tested in three different CBS/sulfur vulcanization systems: conventional (C.V), semi-efficient (semi-E.V.) and efficient (E.V.). In addition to BCI-MP and BCI-C6 a comparative HVA-2®-containing example was employed.

The rubber formulations which were employed with C.V. are given in Table 10. Similarly lettered examples employed the same quantities of all the ingredients except for the vulcanization accelerator and sulfur contents. The amounts of vulcanization accelerator and sulfur in the rubber formulations considered to be semi-E.V. are given in Table 11. The amounts of vulcanization accelerator and sulfur in the rubber formulations considered to be E.V. are given in Table 12.

TABLE 10

| Example | 21a | 22a | Ja |
|---|---|---|---|
| Compound | | | |
| Natural Rubber | 100 | 100 | 100 |
| Carbon Black | 50 | 50 | 50 |
| Zinc Oxide | 5 | 5 | 5 |
| Resin Pine Tar | 2 | 2 | 2 |
| BCI-MP | 1.5 | — | — |
| BCI-C6 | — | 1.5 | — |
| HVA-2 ® | — | — | 1.3 |
| CBS | 0.6 | 0.6 | 0.6 |
| Sulfur | 2.3 | 2.3 | 2.3 |

TABLE 11

| Example | 21b | 22b | Jb |
|---|---|---|---|
| Compound | | | |
| CBS | 1.5 | 1.5 | 1.5 |
| Sulfur | 1.5 | 1.5 | 1.5 |

TABLE 12

| Example | 21c | 22c | Jc |
|---|---|---|---|
| Compound | | | |
| CBS | 4.0 | 4.0 | 4.0 |
| Sulfur | 0.5 | 0.5 | 0.5 |

To obtain the results given in Table 13, vulcanization was carried out at 180° C. over a period of 60 minutes. The anti-reversion effect can be seen by comparing the final torque ($T_f$) with the initial torque maximum ($T_i$).

TABLE 13

| torque (dNm) | $T_i$ | $T_r$ |
|---|---|---|
| Example | | |
| 21a | 16.25 | 19 |
| 22a | 16.25 | 18.8 |
| Ja | 19.5 | 15.0 |
| 21b | 17.8 | 18.8 |
| 22b | 17.5 | 18.0 |
| Jb | 21.6 | 16.0 |
| 21c | 13.7 | 17.5 |
| 22c | 13.0 | 13.5 |
| Jc | 16 | 13.5 |

The compensation effects of the anti-reversion agents according to the present invention were quite similar in C.V. and semi-E.V., but decreased for the efficient cure system. HVA-2® showed vulcanization curves initially reflecting high reactivity, but due to reversion a low final torque resulted. Compared with the anti-reversion agents of the present invention the contribution of HVA-2® to the cure curves was relatively less dependent on the efficiency of the cure system.

BCI-MP and BCI-C6 have a significant anti-reversion effect in C.V. and semi-E.V. NR-based formulations. The effect on E.V compounds is smaller, but also less relevant in E.V compounds. The anti-reversion effect of BCI's is probably a synergistic effect with sulfur. HVA-2® shows inferior anti-reversion effects in the cure curves as compared with the anti-reversion agents of the present invention.

EXAMPLES 23–27

The effect of mixed itaconimide and citraconimide groups was tested for hexamethylene bisimide derivatives (BI-C6). Also the bis-itaconimide of diphenylmethane (BII-DPM) was compared with the bis-citracon imide thereof (BCI-DPM). The rubber formulations which were employed are given in Table 14.

TABLE 14

| Example No. | 23 | 24 | 25 | 26 | 27 |
|---|---|---|---|---|---|
| Compound | | | | | |
| Natural Rubber | 100 | 100 | 100 | 100 | 100 |
| Carbon Black | 50 | 50 | 50 | 50 | 50 |
| Stearic Acid | 2 | 2 | 2 | 2 | 2 |
| Zinc Oxide | 5 | 5 | 5 | 5 | 5 |
| Resin Pine Tar | 3 | 3 | 3 | 3 | 3 |
| CBS | 0.6 | 0.6 | 0.6 | 0.6 | 0.6 |
| Sulphur | 2.3 | 2.3 | 2.3 | 2.3 | 2.3 |
| BI(97,5/2.5)[1]-C6 | 1.5 | — | — | — | — |
| BI(70/30)[1]-C6 | — | 1.5 | — | — | — |
| BI(37/63)[1]-C6 | — | — | 1.5 | — | — |
| BCI-DPM | — | — | — | 1.9 | — |
| BII-DPM | — | — | — | — | 1.9 |

[1]The relative citraconimide/itaconimide content (mole %/mole %) is given in parentheses.

To obtain the results given in Table 15, vulcanization was carried out at 180° C. over a period of 60 minutes. The anti-reversion effect can be seen by comparing $T_f$ with $T_i$.

TABLE 15

| torque (dNm) | $T_i$ | $T_r$ |
|---|---|---|
| Example | | |
| 23 | 16 | 17.6 |
| 24 | 16 | 17.6 |
| 25 | 16 | 17.6 |
| 26 | 16.3 | 20.5 |
| 27 | 17.4 | 18.5 |

The different hexamethylene citraconimide derivatives with itaconimide contents of 2.5%, (BCI-C6), 30%, and 63%, respectively, gave similar vulcanization curves. The diphenylmethane derivatives of BCI and BII showed anti-reversion effects close to those of BCI-MP. The BII-DMP showed an improved modulus after vulcanization at 180° C.

EXAMPLES 28–35

The effects of BCI-MP on the physical properties of natural rubber, styrene-butadiene rubber (SBR) and different rubber blends (e.g NR-BR and SBR-BR, NR being natural rubber and BR being butadiene rubber) were investigated.

The formulations of the NR and SBR compounds are listed in Table 16.

TABLE 16

| Example No. | 28 | 29 | 30 | 31 |
|---|---|---|---|---|
| Compounds | | | | |
| NR | 100 | 100 | — | — |
| SBR | — | — | 100 | 100 |
| Carbon Black | 50 | 50 | 50 | 50 |
| Stearic acid | 2 | 2 | 2 | 2 |
| Zinc Oxide | 5 | 5 | 5 | 5 |
| Aromatic oil A[1] | — | — | 3 | 3 |
| Aromatic oil B[2] | 3 | 3 | — | — |
| BCI-MP | — | 1.5 | — | 1.5 |
| CBS | 0.6 | 0.6 | 0.6 | 0.6 |
| Sulfur | 2.3 | 2.3 | 2.3 | 2.3 |

[1]= aromatic oil Dutrex 729 HP ®
[2]= aromatic oil Enerflex 72 ®

The formulations of the NR-BR and SBR-BR blends are listed in Table 17.

TABLE 17

| Example No. | 32 | 33 | 34 | 35 |
|---|---|---|---|---|
| Compounds | | | | |
| NR | 80 | 80 | — | — |
| SBR | — | — | 55 | 55 |
| BR | 20 | 20 | 45 | 45 |
| Carbon Black | 50 | 50 | 50 | 50 |
| Stearic Acid | 2 | 2 | 2 | 2 |
| Zinc Oxide | 5 | 5 | 5 | 5 |
| Aromatic oil A | 3 | 3 | 3 | 3 |
| BCI-MP | — | 1.5 | — | 1.5 |
| CBS | 0.6 | 0.6 | 0.6 | 0.6 |
| Sulfur | 2.3 | 2.3 | 2.3 | 2.3 |

Mixing Procedure for the Blend

In a banbury mixer separate rubber masterbatches were mixed to ensure homogeneous carbon dispersion.

The additional ingredients, including BCI-MP, were added to the masterbatch according to the formulations of Table 17 and mixed. After 24 hours the masterbatches were cross-blended in the banbury mixer for 3 minutes. After an additional 24 hours, the batches were finalized on a mill on addition of sulfur and accelerators.

The cure characteristics of the examples obtained at 150° C. are listed in Table 18 and the values obtained at 180° C. are presented in Table 19. At the optimum cure time (opt. cure time ($t_{90}$)) the torque was at its maximum. At the reversion time the torque started to decrease.

TABLE 18

| Characteristics | Cross-linking R∞, dNm | Scorch safety $t_s2$, min | Opt. cure time, min | Reversion time, min |
|---|---|---|---|---|
| Example | | | | |
| 28a | 18.5 | 4.1 | 11.0 | 24.3 |
| 29a | 18.7 | 4.2 | 12.4 | — |
| 30a | 20.7 | 10.1 | 24.1 | — |
| 31a | 22.6 | 10.4 | 24.3 | — |
| 32a | 20.4 | 4.9 | 12.8 | 28.8 |
| 33a | 20.1 | 4.8 | 13.0 | — |
| 34a | 23.6 | 9.4 | 26.2 | — |
| 35a | 23.7 | 9.7 | 26.0 | — |

TABLE 19

| | | | | |
|---|---|---|---|---|
| 28b | 15.3 | 0.6 | 1.6 | 2.3 |
| 29b | 15.2 | 0.6 | 1.7 | — |
| 30b | 20.5 | 1.2 | 4.3 | 12.5 |
| 31b | 22.8 | 1.2 | 27 | — |
| 32b | 17.1 | 0.6 | 1.9 | 3.1 |
| 33b | 16.4 | 0.6 | 7.9 | — |
| 34b | 27.1 | 1.0 | 4.0 | 20.2 |
| 35b | 22.5 | 1.1 | 5.5 | — |

— indicates no reversion

Tables 20 and 21 give the resulting properties of the cured products obtained, a-indices referring to curing at 150° C. up to optimal cure, $t_{90}$ and b-indices referring to curing at 180° C. over a period of 60 minutes.

TABLE 20

| Example No. | 28a | 28b | 29a | 29b | 30a | 30b | 31a | 31b |
|---|---|---|---|---|---|---|---|---|
| Properties | | | | | | | | |
| Hardness, Shore A, MPa | 61 | 42 | 53 | 51 | 67 | 66 | 69 | 69 |
| Modulus, MPa | | | | | | | | |
| 50% | 0.95 | 0.64 | 0.97 | 0.96 | 1.86 | 1.65 | 1.89 | 1.96 |
| 100% | 1.63 | 0.96 | 1.66 | 1.68 | 3.66 | 2.92 | 3.53 | 4.01 |
| 300% | 8.33 | 4.59 | 8.45 | 8.76 | 20.1 | 16.1 | 18.9 | 21.5 |
| Tensile Strength, MPa | 25.6 | 13.5 | 24.8 | 15.8 | 29.5 | 21.4 | 26.6 | 22.9 |
| Elongation at break, % | 590 | 545 | 595 | 429 | 423 | 387 | 379 | 294 |

TABLE 21

| Example No. | 32a | 32b | 33a | 33b | 34a | 34b | 35a | 35b |
|---|---|---|---|---|---|---|---|---|
| Properties | | | | | | | | |
| Hardness, Shore A, MPa | 67 | 61 | 67 | 69 | 67 | 64 | 67 | 69 |
| Modulus, MPa | | | | | | | | |
| 50% | 1.61 | 1.29 | 1.49 | 1.75 | 1.53 | 1.47 | 1.56 | 1.75 |
| 100% | 3.09 | 2.22 | 2.67 | 3.29 | 2.49 | 2.40 | 2.51 | 3.06 |
| 300% | 15.4 | 11.1 | 13.5 | 15.9 | 12.9 | 12.5 | 12.4 | 16.2 |
| Tensile Strength, MPa | 27.2 | 17.4 | 29.7 | 20.5 | 22.0 | 20.9 | 20.9 | 19.0 |
| Elongation at break, % | 503 | 417 | 513 | 389 | 454 | 458 | 442 | 313 |

As already shown in previous examples, BCI-MP has a remarkable effect by counteracting the reversion phenomenon in NR formulations. This is also true for SBR, NR-BR and SBR-BR formulations. The mechanical properties of the SBR, NR-BR and SBR-BR vulcanizates with BCI-MP are well retained, especially on over-cure.

EXAMPLES 36–41

Tire formulations with common ingredients were prepared employing various BCI-MP contents. A truck tire tread compound recipe according to "C.S.L. Baker c.s., Elastomerics, July 1989, pp 20–25" is listed in Table 22, example 36. Various BCI-contents were added to this composition (examples 37–41). The resulting mechanical properties obtained by vulcanization at 150° C. up to optimum cure, are given in Table 23, the ones obtained by vulcanization at 180° C. overcured for 60 minutes, in Table 24.

TABLE 22

| Example No. | 36 | 37 | 38 | 39 | 40 | 41 |
|---|---|---|---|---|---|---|
| Compound | | | | | | |
| NR | 80 | 80 | 80 | 80 | 80 | 80 |
| BR | 20 | 20 | 20 | 20 | 20 | 20 |
| Carbon Black | 55 | 55 | 55 | 55 | 55 | 55 |
| Stearic Acid | 2 | 2 | 2 | 2 | 2 | 2 |
| Zinc Oxide | 4 | 4 | 4 | 4 | 4 | 4 |
| Aromatic oil A | 8 | 8 | 8 | 8 | 8 | 8 |
| Permanax 6PPD ® | 2 | 2 | 2 | 2 | 2 | 2 |
| BCI-MP | — | 0.5 | 0.75 | 1.00 | 1.25 | 1.50 |
| CBS | 1.2 | 1.2 | 1.2 | 1.2 | 1.2 | 1.2 |
| Sulfur | 1.2 | 1.2 | 1.2 | 1.2 | 1.2 | 1.2 |

TABLE 23

| Example No | 36a | 37a | 38a | 39a | 40a | 41a |
|---|---|---|---|---|---|---|
| Properties | | | | | | |
| Hardness, Sh A | 60 | 62 | 62 | 63 | 63 | 64 |
| Modulus | | | | | | |
| 50% | 1.17 | 1.14 | 1.15 | 1.14 | 1.20 | 1.14 |
| 100% | 2.05 | 1.92 | 1.91 | 1.88 | 2.04 | 1.95 |
| 300% | 10.8 | 10.3 | 10.6 | 10.4 | 10.8 | 10.8 |
| Tensile Strength, MPa | 24.0 | 25.1 | 24.7 | 24.2 | 24.0 | 23.2 |
| Elongation at break, % | 556 | 600 | 571 | 574 | 568 | 535 |
| Tear strength, N/mm | 119 | 107 | 114 | 110 | 110 | 111 |

TABLE 24

| Example No. | 36b | 37b | 38b | 39b | 40b | 41b |
|---|---|---|---|---|---|---|
| Properties | | | | | | |
| Hardness, Sh A | 55 | 60 | 62 | 64 | 63 | 66 |
| Modulus | | | | | | |
| 50% | 1.02 | 1.07 | 1.19 | 1.33 | 1.35 | 1.32 |
| 100% | 1.65 | 1.71 | 1.82 | 2.37 | 2.37 | 2.30 |
| 300% | 8.5 | 8.8 | 10.0 | 11.9 | 12.0 | 11.5 |
| Tensile Strength, MPa | 16.5 | 18.3 | 20.4 | 20.7 | 20.6 | 20.4 |
| Elongation at break, % | 482 | 502 | 501 | 489 | 461 | 460 |
| Tear strength, N/mm | 41 | 60 | 64 | 66 | 66 | 68 |

These experiments show that BCI-MP can be used in various quantities to improve the reversion resistance of tire compounds.

EXAMPLE 42

Structural Characterization of Rubber Networks

NR gum stocks (NR 100 parts, zinc oxide 5 phr, stearic acid 2 phr, CBS 0.6 phr and sulfur 2.3 phr) were compounded with various coagents: phenylmaleimide (PMI), HVA-2®, phenylcitraconimide (PCI) and BCI-MX (all 1.5 phr). The compounds were vulcanized at 150° C. until optimum cure ($t_{90}$) and at 170° C. for 30 min. The number and distribution of types of crosslinks were determined as described above and presented in TABLES 25 and 26.

TABLE 25

Distribution of crosslinks in vulcanizates obtained at 150° C. cured up to $t_{90}$.

| Compound | Total crosslinks* × $10^{*5}$ | Poly Sulfidic × $10^{*5}$ | Disulfidic × $10^{*5}$ | Monosulfidic × $10^{*5}$ | C-C Crosslinks × $10^{*5}$ |
|---|---|---|---|---|---|
| Control | 5.05 | 3.18 (63%) | 1.87 (37%) | — | — |
| HVA-2® | 6.30 | 2.91 (46%) | 1.64 (26%) | 0.17 (3%) | 1.57 (25%) |
| PMI | 5.42 | 3.20 (59%) | 1.96 (36%) | — | 0.26 (5%) |

TABLE 25-continued

Distribution of crosslinks in vulcanizates obtained at 150° C. cured up to $t_{90}$.

| Compound | Total crosslinks* × $10^{*5}$ | Poly Sulfidic × $10^{*5}$ | Disulfidic × $10^{*5}$ | Monosulfidic × $10^{*5}$ | C-C Crosslinks × $10^{*5}$ |
|---|---|---|---|---|---|
| PCI | 4.92 | 3.18 (65%) | 1.75 (35%) | — | — |
| BCI-MX | 5.04 | 2.94 (58%) | 2.10 (42%) | — | — |

*Concentration of crosslinks are expressed in terms of Gram mole per gram of RH.

TABLE 26

Distribution of crosslinks of vulcanizates obtained at 170° C. and overcured for 30 minutes

| Compound | Total crosslinks* × $10^{*5}$ | Poly Sulfidic × $10^{*5}$ | Disulfidic × $10^{*5}$ | Monosulfidic × $10^{*5}$ | C-C Crosslinks × $10^{*5}$ |
|---|---|---|---|---|---|
| Control | 2.05 | 0.04 (2%) | 0.06 (5%) | 1.94 (93%) | — |
| HVA-2® | 2.2 | 0.11 (5%) | 0.11 (5%) | 1.32 (60%) | 0.67 (30%) |
| PMI | 2.12 | 0.008 (2%) | 0.03 (91%) | 1.93 (91%) | 0.15 (7%) |
| PCI | 1.86 | 0.05 (3%) | 0.10 (5%) | 1.71 (92%) | — |
| BCI-MX | 2.54 | 0.03 (1%) | 0.10 (4%) | 0.88 (35%) | 1.53 (60%) |

*Concentration of crosslinks are expressed in terms of Gram mole per gram of RH.

After optimum cure at 150° C. only PMI and BMI-MP gave an increased number of total crosslinks as compared to the control which consisted besides sulfidic also of non-sulfidic carbon-carbon type crosslinks. Similarly cured compounds with PCI and BCI-MX showed no additional contribution to the total crosslinks and no C-C type crosslinks.

These results indicate that coagents such as biscitraconimides have substantially no influence on the total crosslink density up to optimal cure in contrast to bismaleimides.

EXAMPLE 43

Extraction Experiments

Sheets of NR gum stock with 1.5 phr HVA-2® or BCI-MP vulcanized at 150° C. until optimum cure were extracted with chloroform in a Soxhlet apparatus over a 24 hour period. The extract was evaporated, dissolved in deuterated chloroform and examined with H-NMR. The extract from the HVA-2® containing sheet did not show a detectable quantity of bismaleimide, whereas BCI-MP was successfully extracted from the sheet containing BCI-MP. This indicates that unreacted BCI-MP was present in the vulcanizate.

EXAMPLE 44

Compounding BCI with Rubber on a Two-roll Mill and in a Banbury Internal Mixer

BCI-MP was compounded with a NR rubber recipe (NR SMR CV5: 100 parts, carbon black N-330 50 phr, stearic acid 2 phr, zinc oxide RS 5 phr, aromatic oil (Dutrex 729

HP®) 3 phr, Perkacit® CBS 0.6 phr and sulfur 2.3 phr) by different procedures;

a. The ingredients, excepting CBS, sulfur and BCI-MP, were mixed in a Banbury internal mixer at 135°–140° C. stepwise for 6 minutes. Then, the vulcanization agents and the BCI-MP (1.5 phr) were mixed on a two-roll mill at 60°–70° C.
b. The ingredients including 1.5 phr BCI-MP and excepting sulfur and CBS, were mixed in the Banbury and the CBS and sulfur were added on a two-roll mill.

Then, the cure characteristics of these compounds and a control compound containing no BCI-MP were determined using a Monsanto rheometer MDR 2000E at 180° C. during a 60 minute period.

Monsanto rheometer data obtained at 150° C. (data in parenthesis are obtained at 180° C.)

There was no difference in anti-reversion effect according to the cure characteristics after either following the two-roll mill or Banbury procedure for compounding.

TABLE 27

|  | Control | Procedure a) | Procedure b) |
|---|---|---|---|
| Scorch safety, $t_s2$ (min) | 11.0 | 12.4 | 12.5 |
|  | (1.6) | (1.7) | (1.6) |
| Cure time, $t_{90}$ (min) | 4.1 | 4.2 | 4.2 |
|  | (0.6) | (0.6) | (0.6) |
| Extent of crosslinking, R∞ (dNm) | 18.5 | 18.7 | 19.3 |
| Monsanto rheometer cure curve at 180° C., 60 min (dNm): |  |  |  |
| $T_i$ | 17.3 | 17.3 | 17.4 |
| $T_f$ | 11.5 | 19.0 | 19.0 |

EXAMPLE 45

Properties of NR/SBR and NR Compounds with BCI-MP

A carbon black-filled NR compound with conventional amounts of activators, processing oil, antidegradants and a C.V. curing system with 1.8 phr sulfur, and an NR/SBR (75/25) blend with conventional amounts of activators, oils, antidegradants, wax and a semi-E.V. curing system with 1.5 phr sulfur were mixed with 0.5 or 1.0 phr BCI-MP according to a standard procedure as described above. In control compounds, BCI-MP was omitted.

Tables 28 and 29 show that there is slight or no influence of BCI-MP on scorch and cure characteristics of the NR/SBR and NR compounds. The reversion time at 170° C. is always increased. A Monsanto rheometer ODR was used for the determination of cure characteristics.

TABLE 28

Scorch and Cure characteristics* of NR-SBR compounds.

| Compound | 1 (control) | 2 (BCI-MP 0.5 phr) | 3 (BCI-MP 1.0 phr) |
|---|---|---|---|
| Mooney scorch time min Cure at 150° C.: | 43 | 42 | 43 |
| Extent of crosslinking, R∞, Nm | 2.53 | 2.50 | 2.45 |
| Scorch safety, $t_s2$, min. | 8.0 | 8.0 | 7.5 |
| Optimum curetime, $t_{90}$, min. | 14.5 | 14.0 | 14.0 |
| Reversion time, $t_r2$, min. | (−) | (−) | (−) |

TABLE 28-continued

Scorch and Cure characteristics* of NR-SBR compounds.

| Compound | 1 (control) | 2 (BCI-MP 0.5 phr) | 3 (BCI-MP 1.0 phr) |
|---|---|---|---|
| Cure at 170° C.: |  |  |  |
| Extent of crosslinking, R∞, Nm | 2.25 | 2.25 | 2.25 |
| Scorch safety, $t_s2$, min. | 2.5 | 2.5 | 2.5 |
| Optimum cure time, $t_{90}$, min. | 5.0 | 5.0 | 5.0 |
| Reversion time, $t_r2$, min. | 23.0 | (−) | (−) |

(−) indicates no reversion
*Monsanto rheometer ODR

TABLE 29

Scorch and Cure* characteristics of NR compounds.

| Compound | 4 (control) | 5 (BCI-MP 0.5 phr) | 6 (BCI-MP 1.0 phr) |
|---|---|---|---|
| Mooney scorch time min Cure at 150° C.: | 41 | 41 | 42 |
| Extent of crosslinking, R∞, Nm | 2.77 | 2.70 | 2.70 |
| Scorch safety, $t_s2$, min. | 5.8 | 6.3 | 6.2 |
| Optimum cure time, $t_{90}$, min. | 13.8 | 14.0 | 14.0 |
| Cure at 170° C.: |  |  |  |
| Extent of crosslinking, R∞, Nm | 2.4 | 2.3 | 2.4 |
| Scorch safety, $t_s2$, min. | 1.6 | 1.7 | 1.9 |
| Optimum cure time, $t_{90}$, min. | 4.1 | 3.9 | 4.3 |
| Reversion time, $t_r2$, min. | 10.5 | 16.4 | (−) |

(−) indicates no reversion
*Monsanto rheometer ODR

TABLES 30 and 31 show improvements obtained in the NR/SBR and NR compounds with BCI-MP regarding hardness, modulus, tensile strength, tear strength, compression set, and abrasion.

TABLE 30

Mechanical properties of the vulcanizates cured at 150° C. for $t_{90}$ and at 170° C. for 30 min. (overcured shown between parenthesis).

| Compound | 1 | 2 | 3 |
|---|---|---|---|
| Hardness, Shore A | 57.0 | 60.0 | 60.0 |
|  | (54.5) | (59.5) | (60.0) |
| Modulus |  |  |  |
| 50%, MPa | 1.20 | 1.15 | 1.20 |
|  | (0.90) | (1.15) | (1.20) |
| 100%, MPa | 1.90 | 1.85 | 1.80 |
|  | (1.35) | (1.81) | (1.90) |
| 300%, MPa | 9.30 | 9.45 | 9.0 |
|  | (6.51) | (8.90) | (9.95) |
| Tensile strength, MPa | 23.2 | 23.1 | 23.3 |
|  | (15.5) | (19.0) | (20.1) |
| Tear strength, KN/m | 89.0 | 86.5 | 82.5 |
|  | (46.5) | (61.5) | (58.5) |
| Compression set, % |  |  |  |
| 24 h/70° C. | 21 | 23 | 22 |
|  | (26) | (25) | (24) |
| 72 h/23° C. | 15 | 14 | 12 |
|  | (20) | (17) | (17) |
| Abrasion (volume loss mm³/40 m path travelled) | 102 | 103 | 105 |
|  | (201) | (131) | (117) |

TABLE 31

Mechanical properties of the vulcanizates cured at 150° C. for $t_{90}$ and at 170° C. for 30 min. (overcured shown in parenthesis).

| Compound | 4 | 5 | 6 |
|---|---|---|---|
| Hardness, Shore A | 60 | 62 | 64 |
|  | (52) | (57) | (60) |
| Modulus |  |  |  |
| 50%, MPa | 1.15 | 1.20 | 1.20 |
|  | (0.88) | (1.04) | (1.20) |
| 100%, MPa | 2.06 | 2.15 | 2.10 |
|  | (1.30) | (1.65) | (2.00) |
| 300%, MPa | 11.8 | 11.4 | 11.4 |
|  | (6.6) | (8.6) | (10.7) |
| Tensile strength, MPa | 27.2 | 28.0 | 28.5 |
|  | (18.2) | (21.3) | (21.3) |
| Tear strength, KN/m | 101 | 119 | 136 |
|  | (25.5) | (39.0) | (58.0) |
| Compression set, % |  |  |  |
| 24 h/70° C. | 21 | 23 | 23 |
|  | (33) | (28) | (24) |
| 72 h/23° C. | 9 | 10 | 23 |
|  | (17) | (13) | (12) |
| Abrasion (volume loss mm³/40 m path travelled) | 122 | 121 | 122 |
|  | (214) | (172) | (145) |

TABLES 32 and 33 show substantial reduction of heat build up (temperature rise) and permanent set in the Goodrich flexometer test and improved fatigue resistance of the compounds containing BCI-MP cured at 170° C. for 30 min.

TABLE 32

Heat build up and permanent set properties of overcured vulcanizates (170° C., 30 minutes)

| a) NR/SBR Compounds | 1 (control) | 2 (BCI-MP 0.5 phr) | 3 (BCI-MP 1.0 phr) |
|---|---|---|---|
| Temperature rise, Δt, °C. | 42 | 30 | 26 |
| Permanent set, % | 12.0 | 8.1 | 5.4 |

| b) NR Compounds | 4 (control) | 5 (BCI-MP 0.5 phr) | 6 (BCI-MP 1.0 phr) |
|---|---|---|---|
| Temperature rise, Δt, °C. | 52 | 31 | 24 |
| Permanent set, % | 17.2 | 8.2 | 5.2 |

TABLE 33

Fatigue to Failure properties of overcured vulcanizates (170° C., 30 minutes)

| a) NR/SBR Compounds | 1 (control) | 2 (BCI-MP 0.5 phr) | 3 (BCI-MP 1.0 phr) |
|---|---|---|---|
| Number of Kilo cycles to Failure | 37.5 | 38.1 | 41.2 |

| (b) NR-Compounds | 4 (control) | 5 (BCI-MP 0.5 phr) | 6 (BCI-MP 1.0 phr) |
|---|---|---|---|
| Number of Kilo cycles to Failure | 50.1 | 53.7 | 55.4 |

Increased loss modulus (E") as measured by dynamic mechanical analysis of the NR/SBR blend with BCI-MP as shown in TABLE 34 can contribute to the improvement of tire properties such as wet grip or skid resistance (K. A. Grosch, Nature, 197, 858, 1963).

TABLE 34

Dynamic-mechanical data (at 20° C.) of NR/SBR vulcanizates cured at 150° C./$t_{90}$.

| Compound | E' MPa | E" MPa | E* MPa | tanδ |
|---|---|---|---|---|
| 1 (Control) | 18.3 | 2.8 | 18.5 | 0.152 |
| 2 (BCI-MP 0.5 phr) | 22.2 | 3.2 | 22.4 | 0.145 |
| 3 (BCI-MP 1.0 phr) | 24.4 | 3.6 | 24.7 | 0.148 |

Increased storage modulus (E') and decreased loss tangent (tanδ) measured at 60° C. as shown in TABLE 35 imply a lower loss compliance (tanδ/E') which can contribute to improved tire properties such as reduced rolling resistance (J. M. Collins et al., Trans. Inst. Rubber Ind. 40, T239, 1964), which by consequence leads to fuel savings during service.

TABLE 35

Dynamic-mechanical data (at 60° C.) of NR-vulcanizates cured at 170° C./30 min.

| Compound | E' MPa | E" MPa | E* MPa | tanδ |
|---|---|---|---|---|
| 4 (Control) | 8.2 | 1.3 | 8.3 | 0.160 |
| 6 (+BCI-MP 1.0 phr) | 9.3 | 1.1 | 9.4 | 0.119 |

EXAMPLE 46

NR/BR Compound with Various BCI's

An NR/BR recipe (see Example 36), useful as truck tire tread compound (C. S. L. Baker c.s., Elastomerics, July 1989, pp.20–25) has been used to test the effects of various BCI's. Compounding was done with 1.0 phr BCI-MP, BCI-DPM and BCI-MX as described above (Example 36). Vulcanization was done by compression moulding at 150° C. ($t_{90}$ and 60 min) and 170° C. ($t_{90}$ and 30 min).

TABLE 36 shows that BCI's have slight or no effect on Mooney viscosity, scorch time and cure characteristics.

TABLE 36

|  | Control | BCI-MP | BCI-DPM | BCI-MX |
|---|---|---|---|---|
| Mooney viscosity (MU) | 46.4 | 42.6 | 45.2 | 45.3 |
| Mooney Scorch time (min) | 36.1 | 36.1 | 36.4 | 35.5 |
| Monsanto rheometer cure data (150° C.) |  |  |  |  |
| $t_s2$ | 5.0 | 5.2 | 5.5 | 5.2 |
| $t_{90}$ | 8.3 | 8.4 | 8.7 | 8.6 |
| Delta torque (Nm) | 1.5 | 1.5 | 1.5 | 1.5 |
| Monsanto rheometer cure data (170° C.) |  |  |  |  |
| $t_s2$ | 1.5 | 1.6 | 1.7 | 1.7 |
| $t_{90}$ | 2.6 | 2.6 | 2.7 | 2.7 |
| Delta torque (Nm) | 1.4 | 1.4 | 1.4 | 1.4 |

TABLE 37 gives Monsanto rheometer torque data obtained at 140° C. with a total cure time of 8 hours that show that antireversion effects are also obtained under these conditions with the BCI's.

TABLE 37

| Compound | torque (dNm) | |
|---|---|---|
| | $T_i$ | $T_f$* |
| Control | 17.5 | 13.4 |
| BCI-MX | 17.2 | 18.3 |
| BCI-MP | 17.3 | 18.0 |
| BCI-DPM | 17.4 | 18.2 |

*Final torque after 8 hours, 140° C.

TABLES 38 and 39 show improvement of the following properties of vulcanisates after overcure at 150° C. for 60 minutes and especially at 170° C. for 30 minutes: hardness, tensile strength, modulus, abrasion, compression set, tear strength, and both permanent set and heat build up.

TABLE 38

Physical and mechanical properties of the vulcanizates cured at 150° C./$t_{90}$ and 150° C./60 min. (between paranthesis):

| Compound | 01 control | 02 BCI-MP | 04 BCI-DPM | 05 BCI-MX |
|---|---|---|---|---|
| Hardness IRHD | 70 | 71 | 74 | 71 |
| | (67) | (72) | (72) | (70) |
| Tensile strength MPa | 25.5 | 25.4 | 24.9 | 26.3 |
| | (21.9) | (22.8) | (22.9) | (23.0) |
| Modulus 50% MPa | 1.2 | 1.3 | 1.3 | 1.3 |
| | (1.1) | (1.3) | (1.3) | (1.3) |
| Modulus 100% MPa | 2.4 | 2.2 | 2.2 | 2.3 |
| | (1.9) | (2.4) | (2.2) | (2.1) |
| Modulus 300% MPa | 12.5 | 12.0 | 11.3 | 12.4 |
| | (10.5) | (12.5) | (11.2) | (11.2) |
| Abrasion mm³ | 93 | 86 | 117 | 96 |
| | (128) | (76) | (78) | (75) |
| Tear strength kN/m | 115 | 106 | 114 | 113 |
| | (88) | (92) | (87) | (80) |
| Permanent set % | 13.1 | 10.6 | 12.5 | 9.4 |
| | (13.9) | (5.3) | (8.0) | (9.9) |
| Heat build up °C | +40 | +29 | +33 | +27 |
| | (+47) | (+27) | (+31) | (+35) |

TABLE 39

Physical and mechanical properties of the vulcanizates cured at 170° C./$t_{90}$.

| Compound | 01 control | 02 BCI-MP | 04 BCI-DPM | 05 BCI-MX |
|---|---|---|---|---|
| Hardness IRHD | 69 | 69 | 72 | 69 |
| | (63) | (70) | (69) | (68) |
| Rebound % | 34 | 33 | 31 | 33 |
| | (31) | (32) | (32) | (31) |
| Tensile strength MPa | 25.1 | 24.5 | 24.0 | 23.8 |
| | (16.8) | (20.9) | (20.8) | (19.7) |
| Modulus 50% MPa | 1.2 | 1.2 | 1.2 | 1.2 |
| | (1.0) | (1.3) | (1.2) | (1.2) |
| Modulus 100% MPa | 2.1 | 2.0 | 2.0 | 2.0 |
| | (1.5) | (2.1) | (2.0) | (2.0) |
| Modulus 300% MPa | 11.2 | 10.8 | 10.7 | 11.0 |
| | (7.6) | (10.7) | (9.8) | (10.2) |
| Abrasion mm3 | 83 | 86 | 93 | 92 |
| | (126) | (113) | (100) | (90) |
| Tear strength kN/m | 105 | 104 | 102 | 110 |
| | (43) | (68) | (70) | (67) |
| FTFT kcycl | 45.2 | 46.2 | 44.0 | 47.7 |
| | (47.9) | (39.2) | (41.9) | (38.5) |
| Permanent set % | 14.0 | 15.7 | 14.6 | 12.4 |
| | (17.9) | (5.4) | (8.7) | (7.1) |
| Heat build up °C | +39 | +36 | +35 | +30 |
| | (+58) | (+29) | (+35) | (+31) |

TABLE 39-continued

Physical and mechanical properties of the vulcanizates cured at 170° C./$t_{90}$.

| Compound | 01 control | 02 BCI-MP | 04 BCI-DPM | 05 BCI-MX |
|---|---|---|---|---|
| Compression set % (72 h., 23° C.) | 11 | 12 | 14 | 14 |
| | (18) | (15) | (16) | (15) |

+The data in the parentheses are the values obtained for the vulcanizates cured at 170° C./30 minutes.

The compound containing 1 phr BCI-MX (and control without BCI) vulcanized at 170° C. for 30 min was subjected to a blow out test in the Goodrich flexometer.

TABLE 40

| | Blow out test results. | |
|---|---|---|
| | Blow out time (hrs) | Temp. rise (°C.) |
| Control | 1.5 | +92 |
| BCI-MX | >10 | +43 |

The results show that the blow out time is substantially lengthened and the heat build up and temperature rise are substantially lowered by BCI-MX.

EXAMPLE 47

1,10-Bis(4-citraconimidobenzoyloxy)decane (BCI-BAE10), Tris(6-citraconimidohexyl)isocyanurate (TCI-AA33) and 1,8-bis(citraconimido)-4-citraconimidomethyloctane (TCI-C6v) were compounded in an NR recipe (see Example 44) and their effects on the Monsanto rheometer cure curves at 170° or 180° C. up to 30 min determined (Table 41):

TABLE 41

| Coagent | BCI-BAE10 | TCI-AA33 | TCI-C9V |
|---|---|---|---|
| Concentration (phr) | 3.0 | 1.0 | 1.0 |
| Test temperature (°C.) | 180 | 170 | 170 |
| Scorch safety, $t_s2$ (min) | 0.8 | 1.0 | 0.9 |
| | (0.7) | (1.1) | (0.9) |
| Optimal cure time, $t_{90}$ (min) | 1.7 | 3.1 | 2.9 |
| | (1.7) | (3.2) | (2.9) |
| Torque retention after 30 min (%) | 109 | 86 | 91 |
| | (68) | (73) | (73) |

Monsanto rheometer MDR 2000E;
Values between parenthesis: control without BCI or TCI
BCI-BAE10, TCI-AA33 and TCI-C9V had slight or no effect on scorch and cure time, but improved reversion resistance of the compound.

EXAMPLE 48

NR Compound Vulcanized with Higher Amount of Sulfur

A black-filled NR compound (NR SMR CV 100, Carbon black N-326 55, Stearic acid 0.5,ZnO 8, Permanax 6PPD® 2, Dutrex 729 HP® 3, Crystex OT 20® 5, Perkacit CBS® 0.7 phr) containing a high amount of (insoluble) sulfur, useful as steel cord skim stock in tire compounding (M. Piertoh and R. Schubart, Kautsch.+Gummi, Kunstst. 43, 385, 1990), was compounded with 1.0 phr BCI-MP or BCI-MX.

The BCI's had practically no influence on cure characteristics at 170° C. (Table 42):

TABLE 42

| | Cure characteristics at 170° C. | | |
|---|---|---|---|
| Compound | 1 | 2 | 3 |
| Coagent | — | BCI-MP | BCI-MX |
| Scorch safety, t$_s$2 (min) | 0.7 | 0.7 | 0.7 |
| Cure time, t$_{90}$ (min) | 2.6 | 2.8 | 2.7 |
| Delta torque (Nm) | 1.8 | 1.8 | 1.9 |

Compounds containing BCI-MP and BCI-MX showed improved mechanical properties after overcure at 170° C. for 30 min as compared to the control without BCI: improved hardness, modulus, tear strength (Table 43):

TABLE 43

| | Mechanical properties after cure at 170° C., t$_{90}$ and 170° C., 30 min (between parenthesis) | | |
|---|---|---|---|
| Compound | 1 | 2 | 3 |
| Coagent | — | BCI-MP | BCI-MX |
| Hardness, Shore A | 59 | 59 | 60 |
| | (53) | (58) | (57) |
| Modulus (MPa) | | | |
| 50% | 1.5 | 1.5 | 1.5 |
| | (1.2) | (1.6) | (1.7) |
| 100% | 2.7 | 2.7 | 2.7 |
| | (1.8) | (2.6) | (2.8) |
| 300% | 11.6 | 12.0 | 11.8 |
| | (7.9) | (10.7) | (12.1) |
| Tear strength, KN/m | 107 | 115 | 103 |
| | (35) | (42) | (42) |

EXAMPLE 49

The contribution of different coagents to the cross-inking reaction of a conventionally cured carbon-black filled NR compound (see Example 44) was tested at 150° C. to 180° C. up to optimum cure. Table 44 shows the cross-linking reaction of BCI-C6, HVA-2® and BCI-MP, expressed as the percentage change in torque at optimum cure per mmole coagent.

TABLE 44

| | Crosslinking reaction of coagents* | | | |
|---|---|---|---|---|
| Coagent | Concn. (phr) | Temp. °C. | torque change at t$_{90}$ % | torque change at t$_{90}$ %/mmole |
| BCI-C6 | 1.5 | 150 | −3.0 | −0.6 |
| | | 180 | −3.0 | −0.6 |
| HVA-2® | 1.5 | 170 | +13.2 | +2.4 |
| | 5.0 | 170 | +112 | +6.0 |
| | 10 | 170 | +249 | +6.7 |
| BCI-MP | 1.5 | 170 | −4.0 | −0.8 |
| | 5.0 | 170 | −1.3 | −0.1 |
| | 10 | 170 | −3.3 | −0.1 |

*Monsanto rheometer MDR 2000E.

Both BCI-C6 and BCI-MP exerted no cross-linking reaction in the conventionally cured carbon-black filled NR compound as measured by torque change at optimum cure, whereas the bismaleimide and HVA-2® exerted a substantial cross-linking reaction.

What is claimed is:

1. A sulfur-vulcanized rubber composition which comprises the vulcanization reaction product of:

A) 100 parts by weight of at least one natural or synthetic rubber;

B) 0.1 to 25 parts by weight of sulfur and/or a sufficient amount of a sulfur donor to provide the equivalent of 0.1 to 25 parts by weight of sulfur; and C) 0.1 to 5.0 parts by weight of a coagent which only partially reacts under sulfur-vulcanization reaction conditions up to optimum cure, and which, after optimum cure, forms cross-links bonded to the sulfur cross-linked rubber by a carbon-carbon linkage at a rate sufficient to compensate for from 10 to 200 percent of the reversion in said rubber composition.

2. The sulfur-vulcanized rubber composition of claim 1 wherein said rubber composition further comprises 0.1 to 8.0 parts by weight of a vulcanization accelerator.

3. The sulfur-vulcanized rubber composition of claim 1 wherein said coagent has a cross-linking efficiency of −2.0 to 2.0% per millimole under sulfur-vulcanization conditions up to optimum cure.

4. The sulfur-vulcanized rubber composition of claim 1 wherein said coagent forms cross-links at a rate sufficient to compensate for from 40–150% of the reversion in said rubber composition.

5. The sulfur-vulcanized rubber composition of claim 1 which comprises 0.1 to 5.0 parts by weight of unreacted coagent after optimum cure.

6. A process for the vulcanization, at a temperature of from 110° to 220° C. for up to 24 hours, of a vulcanizable composition comprising at least one natural or synthetic rubber in the presence of 0.1 to 25 parts by weight of sulfur or a sufficient amount of a sulfur donor to provide the equivalent of 0.1 to 25 parts by weight of sulfur, wherein said process is carried out in the presence of an effective amount of an anti-reversion coagent which only partially reacts under sulfur-vulcanization reaction conditions up to optimum cure, and which, after optimum cure, forms cross-links bonded to the sulfur cross-linked rubber by a carbon-carbon linkage at a rate sufficient to compensate for from 10 to 200 percent of the reversion in said rubber composition.

7. The vulcanization process of claim 6, wherein said rubber is vulcanized in the further presence of 0.1 to 8.0 parts by weight of a vulcanization accelerator.

8. The vulcanization process of claim 6 wherein said coagent has a cross-linking efficiency of −20 to 2.0% per millimole under sulfur-vulcanization conditions up to optimum cure.

9. The vulcanization process of claim 6 wherein said coagent forms cross-links at a rate sufficient to compensate for from 40–150% of the reversion in said rubber composition.

10. A method for inhibiting the reversion of a rubber composition prepared in a sulfur-vulcanization process which comprises carrying out said sulfur-vulcanization process in the presence of at least one anti-reversion coagent selected from compounds which only partially react under sulfur-vulcanization reaction conditions up to optimum cure, and which, after optimum cure, form cross-links bonded to the sulfur cross-linked rubber by a carbon-carbon linkage at a rate sufficient to compensate for from 10 to 200 percent of the reversion in said rubber composition.

11. The method of claim 10 wherein said coagent has a cross-linking efficiency of −2.0 to 2.0% per millimole under sulfur-vulcanization conditions up to optimum cure.

12. The method of claim 10 wherein said coagent forms cross-links at a rate sufficient to compensate for from 40–150% of the reversion in said rubber composition.

13. An article of manufacture comprising a rubber vulcanized by the process of claim 6.

14. A tire comprising a rubber vulcanized by the process of claim 6.

* * * * *